United States Patent [19]

Lawter et al.

[11] Patent Number: 5,001,139

[45] Date of Patent: Mar. 19, 1991

[54] ENCHANCERS FOR THE TRANSDERMAL FLUX OF NIVADIPINE

[75] Inventors: James R. Lawter, Goshen, N.Y.; John M. Pawelchak, Park Ridge, N.J.

[73] Assignee: American Cyanamid Company, Stamford, Conn.

[21] Appl. No.: 61,934

[22] Filed: Jun. 12, 1987

[51] Int. Cl.$^5$ .................... A61K 31/00; A61K 31/44; A61F 13/00
[52] U.S. Cl. ................................. 514/344; 514/946; 514/947; 424/449
[58] Field of Search ............... 424/449; 514/946, 947, 514/344, 356

[56] References Cited

U.S. PATENT DOCUMENTS

| | | |
|---|---|---|
| 4,284,634 | 8/1981 | Satu . |
| 4,338,322 | 7/1982 | Satu . |
| 4,537,898 | 8/1985 | Hoff et al. ........................... 514/356 |
| 4,685,911 | 8/1987 | Konno et al. ........................ 424/450 |

FOREIGN PATENT DOCUMENTS

| | | |
|---|---|---|
| 0131228 | 7/1984 | European Pat. Off. . |
| 0153200 | 2/1985 | European Pat. Off. . |
| 0186027 | 12/1985 | European Pat. Off. . |
| 58-177916 | 10/1983 | Japan . |
| 59-23673 | 2/1984 | Japan . |
| 59-39827 | 3/1984 | Japan . |
| 59-175415 | 10/1984 | Japan . |
| 59-251037 | 11/1984 | Japan . |

OTHER PUBLICATIONS

Patent Abstracts of JP-vol. 10, No. 166 (C-353) (2222), 13th Jun. 1986; and JP-A- 61 18717 (Nichiban).

*Primary Examiner*—Lester L. Lee
*Assistant Examiner*—Carmen Pili-Curtis
*Attorney, Agent, or Firm*—Thomas S. Szatkowski

[57] ABSTRACT

The transdermal flux rates of 1,4-dihydropyridine derivatives, such as nilvapidine and its enantiomers may be increased by the use of a solvent vehicle which comprises dioctyl adipate, isopropyl myristate, benzyl alcohol, diisopropyl adipate, a mixture of 5 to 50% ethyl alcohol and 95-50% of diisopropyl adipate, or a mixture of any of the foregoing.

11 Claims, No Drawings

ENCHANCERS FOR THE TRANSDERMAL FLUX OF NIVADIPINE

FIELD OF THE INVENTION

This invention is concerned with providing agents that enhance the transdermal flux of certain 1,4-dihydropyridine drugs and compositions of such flux enhancing agents and certain 1,4-dihydropyridine drugs.

BACKGROUND OF THE INVENTION

A transdermal delivery system is a pharmaceutical composition of matter which is applied to the skin in order to deliver the pharmaceutical through the skin to achieve a systemic therapeutic effect as distinguished from a local therapeutic effect.

If a drug exhibits transdermal fluxes that are too low to provide therapeutic plasma concentrations, a flux enhancer may be used to increase transdermal flux. The flux enhancer is a substance, usually a solvent or vehicle that is applied to the skin in combination with a drug to increase the transdermal flux of the drug. Flux enhancers are also known as percutaneous absorption promoters; flux promoters or permeation enhancers. Enhancers are believed to function by disrupting the barrier of the skin or by changing the partitioning behavior of the drug in the skin. In general, an enhancer is specific for a particular type of drug and it may not be useful with every drug. Japanese published patent application No. 59-23673 of Feb. 10, 1984, discloses the use of substances such as propylene glycol, triethylene glycol, polyethylene glycols, ethyl alcohol, salicylic acid, dimethyl sulfoxide, dimethyl acetamide, urea, diethyl sebacate, propylene carbonate, N-methyl pyrrolidone, lanolin or mineral oil components of a transermal delivery systems for dihydro pyridines. Japanese published patent application No. 59-251037 of Nov. 27, 1984, discloses the use of certain pyrrolidones and imidazolinones as transcutaneous flux enhancers for 1,4-dihydropyridine derivatives.

Japanese published patent application No. 59-175415 describes various absorption promoting agents for nifedipine. These agents include lanolin, dimethyl sulfoxide, N-methyl-2-pyrrolidone, dodecyl bromide and diethyl sebacate. Japanese published patent application No. 58-177916 discloses the topical use of solvents such as benzyl benzoate, diisopropyl adipate, benzyl alcohol, N-methyl-2-pyrrolidone and crotamitnon for nifedipine and nicardipine. Japanese published patent application No. 59-39827 discloses the topical administration of nifedipine using auxiliary substances such as propylene glycol, ethylene glycol, ethanol, salicylic acid, urea dimethyl acetamide, dimethyl formamide, diethyl sebacate, lanolin and various surface active agents.

Applicants' have now surprisingly discovered that the transdermal flux rate of certain 1,4-dihydropyridine derivatives of the formula

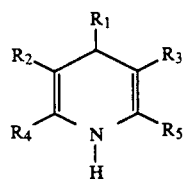

wherein $R_1$, $R_2$, $R_3$, $R_4$, and $R_5$ are hereafter defined, may be increased by the use of solvent vehicles consisting of esters of $C_{12}-C_{18}$ fatty acids with $C_1-C_6$ straight and branched chain alcohols; diesters of aliphatic diacids of the formula

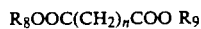

$$R_8OOC(CH_2)_nCOO\ R_9$$

wherein n is a whole integer from 2–8; $R_8$ and $R_9$ may be the same or different and are selected from the group consisting of $C_2$ to $C_{12}$ straight and branched chain alcohols; and compounds of the formula

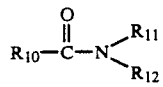

wherein $R_{10}$ is a $C_7-C_{13}$ alkyl or alkenyl group $R_{11}$ and $R_{12}$ are the same or different and are selected from —CH$_2$CH$_2$OH and —CH$_2$CH$_2$CH$_2$—OH; benzyl alcohol, 2-phenylethanal or mixtures thereof with ethyl alcohol.

SUMMARY OF THE INVENTION

According to the present invention, there are provided compositions which comprise certain 1,4-dihydropyridine compounds and a flux enhancer selected from the group consisting of esters of $C_{12}-C_{18}$ fatty acids with $C_1-C_6$ straight and branched chain alcohols; diesters of aliphatic diacids of the formula

$$R_8OOC(CH_2)_nCOO\ R_9$$

wherein n is a whole integer from 2–8; $R_8$ and $R_9$ may be the same or different and are selected from the group consisting of $C_2$ to $C_{12}$ straight and branched chain alcohols; and compounds of the formula

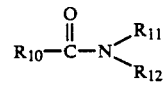

wherein $R_{10}$ is a $C_7-C_{13}$ alkyl or alkenyl group $R_{11}$ and $R_{12}$ are the same or different and are selected from hydrogen —CH$_2$CHOHCH$_3$ and —CH$_2$CH$_2$CH$_2$—OH; benzyl alcohol, 2-phenylethanol, ethanol or mixtures thereof with ethyl alcohol or mineral oil.

Also provided by the invention are methods for enhancing the transdermal flux of a 1,4-dihydropyridine derivative which comprises contacting the skin of a patient in need of treatment with a composition as above defined.

DETAILED DESCRIPTION OF THE INVENTION

Suitable 1,4-dihydropyridines that may be utilized in the practice of the invention include nilvadapine, its enantiomers or its mixtures of enantiomers. These types of compounds are described in U.S. Pat. No. 4,338,322, which is incorporated by reference.

The preferred 1,4-dihydropyridines are of the general formula:

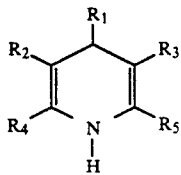

or a resolved enantiomer thereof, wherein
R₁ is aryl which may have one or more suitable substituents(s) or a heterocyclic group,
R₂ and R₃ are each, same or different, esterified carboxy, and
R₄ and R₅ are each hydrogen, cyano, lower alkyl, or substituted lower alkyl in which the substituent is cyano, hydroxy, acyloxy, hydroxyimino, hydrazino, lower alkoxyimino, hydroxy(lower)alkylimino, N'- or N',N'-di(lower)alkylamino(lower)alkylimino, hydrazino, hydroxy(lower)alkylamino, N'- or N',N'-di(lower)alkylamino(lower)alkylamino, a 5 or 6-membered saturated N-containing heterocyclic-lyl which may have hydroxy, lower alkyl or hydroxy(lower)alkyl, or oxo wherein the thus formed carbonyl may be protected with suitable protecting group; provided that, when one of R₄ and R₅ is hydrogen or lower alkyl, the other is always cyano or said substituted lower alkyl, and when R₄ and R₅ are not hydrogen or lower alkyl, both of them are a group selected from cyano and said substituted lower alkyl,
or R₄ is hydrogen or lower alkyl and R₃ and R₅ are combined to form a group of the formula:

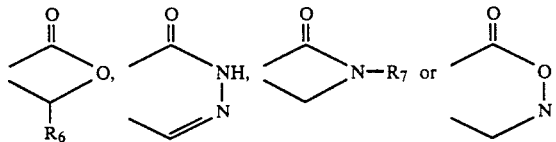

wherein R₆ is hydrogen or methyl and R₇ is 2-(N,N-diethylamino)ethyl or 2-hydroxyethyl.

The terms used in the definitions of the symbols of the general formulae given in this specification and claims are explained as follows:

The term "lower" used in connection with an alkylene, alkyl and alkenyl is intended to mean the one having 1 or 2 to 8 carbon atoms.

The aryl and aryl moieties may be phenyl, naphthyl, xylyl, tolyl, mesityl, cumenyl and the like, which may have one or more suitable substituent(s). Preferred examples of the suitable substituent(s) are halogen, nitro, hydroxy, halo(lower)-alkyl, lower alkoxy, lower alkenyloxy, cyano, lower alkoxycarbonyl or lower alkylsulfamoyl. The halogen or halo moieties are fluorine, chlorine, bromine or iodine.

Lower alkylene moieties may have a straight or branched and saturated bivalent hydrocarbon chain such as methylene, ethylene, methylmethylene, trimethylene, propylene or tetramethylene.

Lower alkyl and lower alkyl moieties may have a straight or branched and saturated hydrocarbon chain such as methyl, ethyl, propyl, isopropyl, butyl, isobutyl, t-butyl, pentyl, neo-pentyl, hexyl, heptyl or octyl.

Lower alkoxy and lower alkoxy moieties may be methoxy, ethoxy, propoxy, isopropoxy, butyoxy, t-butoxy and pentyloxy.

Halo(lower)alkyl moieties may be mono-halo(lower)alkyl such as chloromethyl, bromomethyl or chloropropyl; dihalo(lower alkyl such as 1,2-dichloroethyl, 1,2-dibromoethyl or 2,2-dichloroethyl; and tri-halo(-lower)alkyl such as trifluoromethyl or 1,2,2,-trichloroethyl.

Lower alkenyl and lower alkenyl moieties may be ones having a straight or branched hydrocarbon chain which contains one or more double bond(s), such as vinyl, allyl, butenyl, butanedienyl or penta-2,4-dienyl.

Acyl and acyl moieties may be lower alkanoyl such as formyl, acetyl, propionyl, butyryl, isobutyryl, valeryl, isovaleryl, pivaloyl; substituted lower alkanoyl, for example, carboxy(lower)-alkanoyl, esterified carboxy(-lower)alkanoyl such as lower alkoxycarbonyl(lower)alkanoyl, Nor N,N-di-substituted amino(lower)alkanoyl such as Nor N,N-di(lower)alkylamino(lower)alkanoyl (e.g. N-methyl-(or N,N-diethyl) aminoacetyl, 1(or2)-[N-ethyl(or N,N-diethyl)amino]proprionyl or 1 (or 2)-[N-methyl-N-ethylamino]propionyl) or N-lower alkyl-N-ar(lower)alkylamino(lower)alkanoyl (e.g. 1-(or 2)-[N-methyl-N-benzylamino]propionyl) or aryloxy(lower)alkanoyl such as phenoxyacetyl, tolyloxyacetyl, 2(or 3 or 4)-chlorophenoxyacetyl, 2-[2(or 3 or 4)-chlorophenoxy]propionyl, 2(or 3 or 4)-nitrophenoxyacetyl or 2(or 3 or 4)methoxyphenoxyacetyl); aroyl such as benzoyl, naphthoyl or toluoyl and the like.

Lower alkoxycarbonyl moieties may be methoxycarbonyl, ethoxycarbonyl, propoxycarbonyl, isopropoxycarbonyl, butoxycarbonyl, t-butoxycarbonyl and the like.

Lower alkylsulfamoyl moieties may be methylsulfamoyl, ethylsulfamoyl, propylsulfamoyl, isopropylsulfamoyl, butylsulfamoyl, pentylsulfamoyl and the like.

A heterocyclic group designated R₁ may be an aromatic heterocyclic group containing one or more hetero atom(s) selected form a nitrogen atom, a sulfur atom and an oxygen atom, for example, thienyl, furyl, pyrrolyl, thiazolyl, thiadiazolyl, tetrazolyl, pyridyl, pyrimidinyl, quinolyl, isoquinolyl, benzothienyl, indolyl or purinyl.

Esterifed carboxy groups designated R₂ and R₃ may be lower alkoxycarbonyl such as methoxycarbonyl, ethoxycarbonyl, propoxycarbonyl, butoxycarbonyl, t-butoxycarbonyl; halo(lower)alkoxycarbonyl such as the haloanalogues of the above-mentioned lower alkoxycarbonyl (e.g., 2-bromoethoxycarbonyl, 2-chloroethoxycarbonyl, 2(or 3)-chloropropoxycarbonyl, 2 (or 3)-bromopropoxycarbonyl, 2,2-dichloroethoxycarbonyl or 2,2,2-trichroloethoxycarbonyl); hydroxy(lower)alkoxycarbonyl such as 2-hydroxyethoxycarbonyl or 2(or 3)-hydroxypropoxycarbonyl; lower alkoxy(lower)alkoxycarbonyl such as 2-methoxyethoxycarbonyl, 2-ethoxyethoxycarbonyl or 2(or 3)-methoxy(or ethoxy)-propoxycarbonyl; aryloxycarbonyl such as phenoxycarbonyl, tolyloxycarbonyl, xylyloxycarbonyl or p-chlorophenoxycarbonyl; ar(lower)alkoxycarbonyl such as benzyloxycarbonyl, p-bromobenzyloxycarbonyl, O-methoxybenzyloxycarbonyl or phenethyloxycarbonyl; ar(lower)alkoxy(lower)alkoxycarbonyl such as 2-(benzyloxyl)ethoxycarbonyl or 2 (or 3)-(benzyloxy)-propoxycarbonyl; aryloxy(lower)alkoxycarbonyl such as 2-(phenoxy)ethoxycarbonyl or 2(or 3)-(phenoxy)-propoxycarbonyl; Nor N,N-(di)-substituted amino(-lower)alkoxycarbonyl such as Nor N,N-(di)-(lower)-alkylamino(lower) alkoxycarbonyl (e.g., 1(or 2)-[N-methyl(or N,N-dimethyl)amino]ethoxycarbonyl, 1(or2)-[N-ethyl(or N,N-diethyl)amino]ethoxycarbonyl, or 1(or 2)-N-methyl-N-ethylamino)ethoxycarbonyl or lower alkyl-N-ar(lower)alkylamino(lower)alkoxycarbonyl (e.g. 2-(N-methyl-N-benzylamino)ethoxycarbonyl) and the like, and further $R_2$ and $R_3$ may be same or different.

Lower alkyl substituted with oxo includes lower alkanoyl such as formyl, acetyl, propionyl, butyryl, isobutyryl, valeryl, isovaleryl or pivaloyl and lower alkanoyl(lower)alkyl such as formylmethyl, acetonyl, 2-formylethyl, 3-formylpropyl or butyrylmethyl. The carbonyl group thereof may be protected with suitable protecting group, and thus protected carbonyl group in this invention means a group given by protecting the carbonyl with conventionally employed protecting group for a carbonyl. Suitable examples of such protected carbonyl groups are acetal, cyclic-acetal, thioacetal, cyclic-thioacetal, cyclicmonothioacetal or acylal types of group. Examples of these lower alkyl groups containing such protected carbonyl group are gen-di-(lower)alkoxy(lower)alkyl (e.g. dimethoxymethyl, 1,1-dimethoxyethyl, diethoxymethyl, dipropoxymethyl, 2,2-diethoxyethyl or 2,2-diethoxypropyl; gem-lower alkylenedioxy(lower)alkyl (e.g. 1,3-dioxolan-2-yl, 2-methyl-1,3-dioxolan-2-yl, 4-methyl-1,3-dioxolan-2-yl, 4,5-dimethyl-1,3-dioxolan-2-yl, 1,3-dioxan-2-yl, 2-methyl-1,3-dioxan-2-yl, 1,3-dioxolan-2-yl-methyl, 2-methyl-1,3-dioxolan-2-yl-methyl or 3-(1,3-dioxolan-2-yl)propyl); gem-di-(lower)alkylthio(lower)-alkyl (e.g., dimethylthiomethyl, 1,1-dimethylthioethyl, diethylthiomethyl or 2,2-O-diethylthioethyl); gem-lower alkylenedithio(lower)alkyl (e.g. 1,3-dithiolan-2-yl, 2-methyl-1,3-dithiolan-2-yl, 4-methyl-1,3-dithiolan-2-yl, 4,5-dimethyl-1,3-dithiolan-2-yl, 1,3-dithian-2-yl, 2-methyl-1,3-dithian-2-yl, 1,3-dithiolan-2-yl-methyl, 2-methyl-1,3-dithiolan-2-ylmethyl or 3-(1,3-dithiolan-2yl)propyl); and gem-di(lower)alkanoyloxy(lower)alkyl (e.g., diacetoxymethyl, 1,1-diacetoxyethyl, dipropionyloxymethyl or 2,2-dipropionyloxyethyl); 5 or 6-membered saturated 1-oxa-3-thioheterocyclic-1-yl-(lower)alkyl (e.g., 1,3-oxathiolan-2-yl, 2-methyl-1,3-oxathiolan-2-yl, 4-methyl-1,3-oxathiolan-2-yl, 4,5-dimethyl-1,3-oxathiolan-2-yl, 1,3-oxothian-2-yl, 2-methyl-1,3-oxothian-2-yl, 1,3-oxathiolan-2-ylmethyl, 2-methyl-1,3-oxathiolan2-ylmethyl or 3-(1,3-oxathiolan-2-yl)propyl).

A 5 or 6-membered saturated N-containing heterocyclic-1-yl) group may be one which may contain additional one or more hetero atom(s) selected from nitrogen, sulfur and oxygen atoms such as pyrrolidin-1-yl, piperidino, imidazolidin-1-yl, morpholino or thiomorpholino, and it may be optionally substituted with hydroxy, lower alkyl or hydroxy(lower)alkyl such as hydroxymethyl, 2-hydroxyethyl, 2-hydroxypropyl or 3-hydroxypropyl.

The other terms of each lower alkoxyimino, N'- or N',N'-di-(lower)alkylamino(lower)alkylimino, hydroxy(lower)alkylamino, N'- or N',N'-di(lower)alkylamino(lower)alkylamino and hydroxy(lower)alkylamino will be clearly defined by applying optionally the above given exemplifications of the terms to them.

Included in this generic formula is 2-cyano-1,4-dihydro-6-methyl-4-(3-nitrophenyl)-3,5-pyridenedicarboxylic acid, 3-methyl-5-(1-methylethyl)ester.

The compositions of the invention may be prepared by admixing the flux enhancer with the drug. The concentration of the drug will depend on the particular drug and the particular enhancer. Generally, solutions of up to and including saturated solutions of the drug may be employed. In addition saturated solutions which contain up to 50% of dispersed, undissolved drug may be used. If desired the flux enhancing agent may be placed in a transdermal patch. In addition other ingredients such as gelling agents, e.g. hydroxypropyl cellulose may be added to form a gel; viscous adhesive agents; polymeric additives, e.g. thickeners; processing agents; stabilizers; preservatives; UV absorbers; antioxidants; viscosity increasing agents and the like may be added.

The $C_{12}$–$C_{18}$ fatty acids used to form the useful esters include lauric, tridecanoic, myristic, pentadecanoic, palmitic, margaric, stearic and the like. The straight and branched chain alcohols used in forming the esters include methanol, ethanol, n-propanol, i-propanol, n-pentanol, n-hexanol and the like.

The diesters include the diesters of succinic, glutamic, adipic, pimelic, suberic, azelaic and sebacic acids with ethanol, n-propanol, iso-propanol, n-hexanol, n-octanol and the like.

Compounds of the formula:

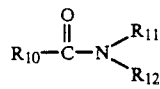

include those where $R_{10}$ is capryl, undecanyl, 3-octenyl, 4-decenyl, 9-decenyl, lauryl or tridecanyl and $R_{11}$ and $R_{12}$ are ethylhydroxy or isopropylhydroxy and hydrogen. The compound N,N-diethylhydroxy lauramide is preferred.

Ethanol may be employed at levels that are sufficient to modify the flux. It may comprise from 10–95% of the total flux enhancer. Light mineral oil or silicone may be employed to control the thermodynamic activity of the flux enhancers. Useful silicones include polydimethyl polysiloxanes. The amount of such materials may be varied to change the rate of absorption of a drug when a particular flux enhancer is employed.

Illustratively, compositions can be provided and used which comprise nilvadipine, 0.01 to 50% by weight with the balance of the composition comprising the flux enhancer alone or with other additives.

DESCRIPTION OF THE PREFERRED EMBODIMENTS

The following examples illustrate the present invention. They are not to be construed to limit the claims in any manner whatsoever.

EXAMPLES 1–11

Saturated solutions of racemic nilvadipine or the (−) and (+) enantiomers and saturated solutions of such materials diluted with mineral oil were prepared in the solvent systems listed in Table 1. The flux rates were determined across split thickness human cadaver skin from the same donor except for example 12. The skin for example 12 was obtained from a different source and is not comparable. The skin is collected from cadaver using a dermatone that is calibrated to obtain a skin thickness of about 400 microns. The cadaver skin is placed in a nutrient medium (Dulbecco's Minimum Essential Medium containing a mycostat and a bacteriostat) on a collagen pad. A disc of skin about 2 cm in diameter is cut and placed in a Bronough transdermal transport cell at 32° C. The dermal surface is contacted with a receptor fluid that consists of polyethylene glycol 400 as a 30% w/w solution in water. The solution of the drug is placed on the skin with a dropper and the flux value is read after steady state conditions have been reached. A carbon-14 radiolabeled drug and a calibrated scintillation counter is used to determine the amount of drug transported. The fluxes were compared to baseline fluxes obtained from a solvent vehicle consisting of 30% aqueous, polyethylene glycol 400 and % of nivadipine.

TABLE 1

| Ex. | nilvadipine | solvent/vehicle | flux micrograms/ $cm^2$/hr | relative rate |
|---|---|---|---|---|
| | racemate* | 30% PEG 400/ water* | 0.005 | 1 |
| 1 | racemate | benzyl alcohol | 0.080 | 16 |
| 2 | racemate | dioctyl adipate | 0.040 | 8 |
| 3 | racemate | isopropyl myristate | 0.150 | 30 |
| 4 | racemate | ethyl alcohol | 0.150 | 30 |
| 5 | racemate | diisopropyl adipate | 0.360 | 72 |
| 6 | racemate | lauramide-DEA | 0.025 | 5 |
| 7 | racemate | 75% diisopropyl adipate in mineral oil | 0.120 | — |
| 8 | racemate | 50% diisopropyl adipate in mineral oil | 0.100 | — |
| | (−) enantiomer* | 30% PEG 400/ water* | 0.028 | 1 |
| | (+) enantiomer* | 30% PEG 400/ water* | 0.028 | 1 |
| 9 | (−) enantiomer | ethanol | 0.580 | 21 |
| 10 | (+) enantiomer | ethanol | 0.560 | 20 |
| 11 | (−) enantiomer | diisopropyl adipate | 0.850 | 30 |
| 12 | (+) enantiomer | diisopropyl adipate | 0.480 | 17 |
| 13 | (−) enantiomer | 10% diisopropyl adipate in ethanol | 0.850 | 30 |

*Control

EXAMPLE 14

If the procedures of Examples 1-13 are repeated substituting other compounds within the scope of formula I for the nilvadipine, flux-enhanced transdermally administrable compositions in accordance with this invention will be obtained.

The foregoing examples demonstrate a dramatic increase in transdermal permeation produced by the selected solvent vehicles Such increase in transdermal permeation permits a biologically active dose of nilvapidine and related compounds to be administered from a transdermal device of much smaller surface area than would otherwise be possible For example, if the total daily dose of nilvadipine were 1 mg, the area required for transdermal application with diisopropyl adipate as flux enhancing agent would be approximately 125 $cm^2$. On the other hand, in accordance with the present state of the art, administration of 1 mg of nilvadipine from a 30% aqueous solution of PEG 400 would require an area of approximately 8000 $cm^2$ which is clearly impractical.

The method or device used for administration of the combination of drug and flux enhancer, may be a semisolid such as an ointment or gel or any other suitable transdermal device.

The drug solution in enhancer may be thickened by the addition of suitable viscosity increasing agents such as polyethylene, or ethylcellulose.

The above-mentioned patents and publications are incorporated herein by reference.

Many variations of the invention will suggest themselves to those skilled in this art in light of the above, detailed description.

All such obvious variations are within the full intended scope of the appended claims.

We claim:

1. A transdermal pharmaceutical composition which consists essentially of the (+) enantiomer of nilvadipine and a flux enhancer which is selected from the group consisting of esters of $C_{12}$-$C_{18}$ fatty acids with $C_1$-$C_6$ straight and branched chain alcohols; diesters of the formula $$R_8OOC(CH_2)_nCOO\ R_9$$

wherein $R_8$ and $R_9$ may be the same or different and are selected from the group consisting of $C_2$-$C_{12}$ straight and branched chain alcohols; compounds of the formula

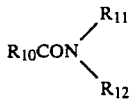

wherein $R_{10}$ is a $C_7$-$C_{13}$ alkyl or alkenyl group; $R_{11}$ and $R_{12}$ are the same or different and are selected from —$CH_2CH_2OH$ and —$CH_2CH_2CH_2OH$; benzyl alcohol; 2-phenyl-ethanol; and mixtures thereof with 10-95% ethanol or mineral oil.

2. A composition as defined in claim 1 wherein said flux enhancer is selected from the group consisting of dioctyl adipate, diisopropyl adipate isopropyl myristate, benzyl alcohol, 2-phenylethanol and mixtures thereof with 10-95% ethanol.

3. A composition as defined in claim 1 wherein the flux enhancer is dioctyl adipate.

4. A composition as defined in claim 1 wherein the flux enhancer is isopropyl myristate.

5. A composition as defined in claim 1 wherein the flux enhancer is benzyl alcohol.

6. A composition as defined in claim 1 wherein the flux enhancer is diisopropyl adipate.

7. A composition as defined in claim 1 wherein the flux enhancer is a mixture of 10-95% of ethyl alcohol and 5-90% of diisopropyl adipate.

8. A method of enhancing the transdermal flux of nilvadipine which comprises contacting the skin of a patient in need of treatment with a composition as defined in claim 1.

9. A method of enhancing the transdermal flux of nilvadipine which comprises contacting the skin of a patient in need of treatment with a composition as defined in claim 2.

10. A composition as defined in claim 1 wherein the said flux enhancer is ethanol.

11. A composition as defined in claim 1 wherein the said flux enhancer is 10% diisopropyl adipate.

* * * * *